(12) United States Patent
Kataoka et al.

(10) Patent No.: US 6,881,484 B2
(45) Date of Patent: Apr. 19, 2005

(54) CORE-SHELL PARTICLE INCLUDING SIGNAL-GENERATING SUBSTANCE ENCLOSED THEREIN AND PROCESS FOR PRODUCING THE SAME

(75) Inventors: Kazunori Kataoka, Tokyo (JP); Yukio Nagasaki, Ibaraki (JP); Naoya Shibata, Chiba (JP); Nobuhiro Hoshino, Tokyo (JP)

(73) Assignees: Mitsubishi Kagaku Iatron, Inc., Tokyo (JP); Nanocarrier Co., Ltd., Chiba (JP)

( * ) Notice: Subject to any disclaimer, the term of this patent is extended or adjusted under 35 U.S.C. 154(b) by 0 days.

(21) Appl. No.: 10/479,247

(22) PCT Filed: May 30, 2001

(86) PCT No.: PCT/JP02/05271

§ 371 (c)(1),
(2), (4) Date: Dec. 1, 2003

(87) PCT Pub. No.: WO02/97430

PCT Pub. Date: May 12, 2002

(65) Prior Publication Data

US 2004/0171771 A1 Sep. 2, 2004

(30) Foreign Application Priority Data

May 30, 2001 (JP) ....................................... 2001-161787

(51) Int. Cl.[7] ................................................ B32B 5/16
(52) U.S. Cl. ....................................... 428/407; 525/902
(58) Field of Search .......................... 428/407; 525/902

(56) References Cited

U.S. PATENT DOCUMENTS 5,395,688 A    3/1995  Shah et al.
6,444,261 B1 *  9/2002  Plaksine et al. ........ 427/213.31

FOREIGN PATENT DOCUMENTS

| EP | 0 305 212 A    | 3/1989  |
| EP | 0 822 217 A    | 2/1998  |
| EP | WO 01/55722 A1 * | 8/2001 |
| JP | 5-262809 A     | 10/1993 |
| JP | 10-195152 A    | 7/1998  |
| JP | 2000-500798 A  | 1/2000  |
| JP | 2001-324507 A  | 11/2000 |
| JP | 2001-66312 A   | 3/2001  |
| JP | 2001-208754 A  | 8/2001  |
| JP | 2002-80903 A   | 3/2002  |

OTHER PUBLICATIONS

Kalinina et al, "A Core–Shell Approach To Producing 3D Polymer Manocomposites" 1999, Macromolecules, American Chemical Society, pp. 4122–4129. (XP–000984727).

* cited by examiner

Primary Examiner—H. Thi Le
(74) Attorney, Agent, or Firm—Sughrue Mion, PLLC

(57) ABSTRACT

A core-shell particle including a signal-generating substance therein, wherein the core-shell particle consists of (1) a core portion substantially made of a water-insoluble polymer compound; and (2) a shell portion substantially made of a water-soluble polymer compound having a reactive functional group, and covering a surface of the core portion in the manner of bristles of a brush; and the core portion and the shell portion are, as a whole, a block copolymer of a water-insoluble polymer and a water-soluble polymer, characterized in that the signal-generating substance is included in the core portion, is disclosed, and a process for producing the same is also disclosed.

The core-shell particle including a signal-generating substance therein is useful as a labeling substance in which neither radioisotopes having handling restrictions nor unstable enzymes are required, a high sensitivity superior to fluorescent substances is achieved, and nonspecific absorption does not occur.

20 Claims, 2 Drawing Sheets

FIG. 1
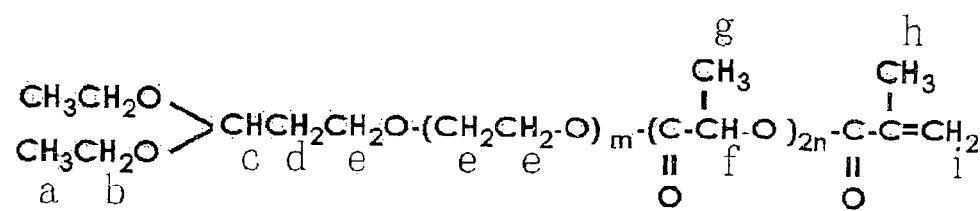
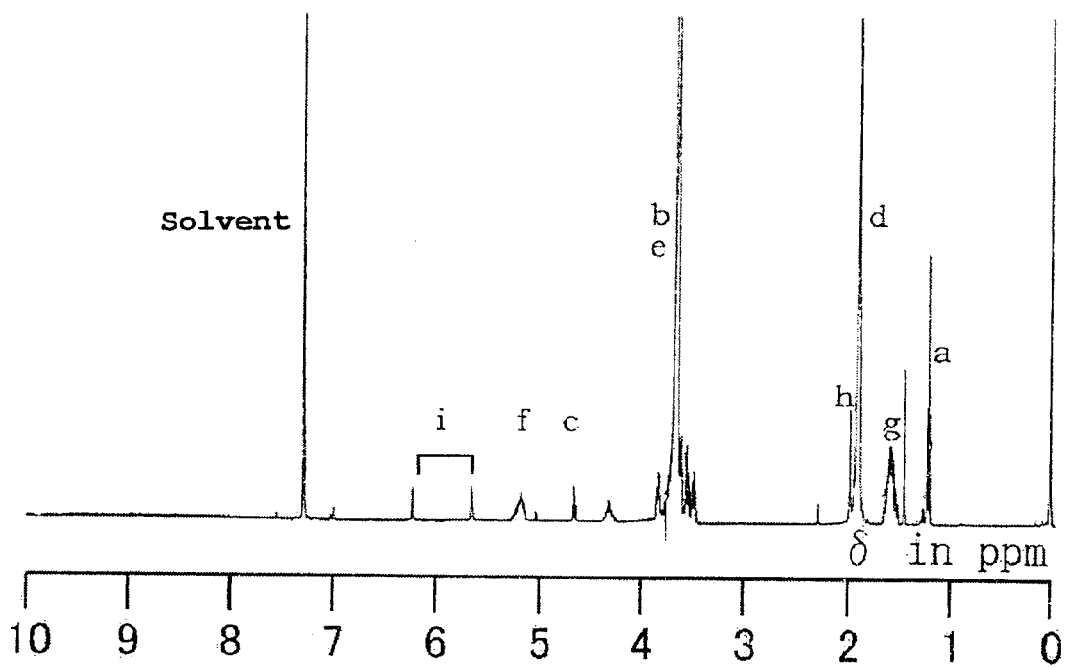
FIG. 2
FIG. 3
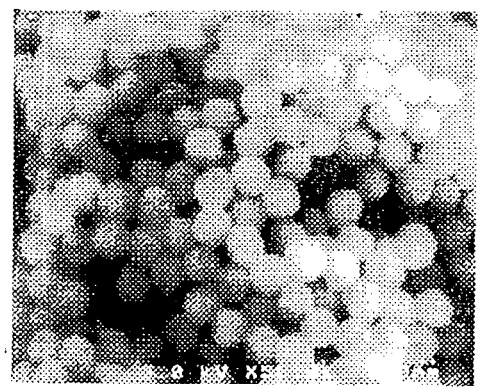
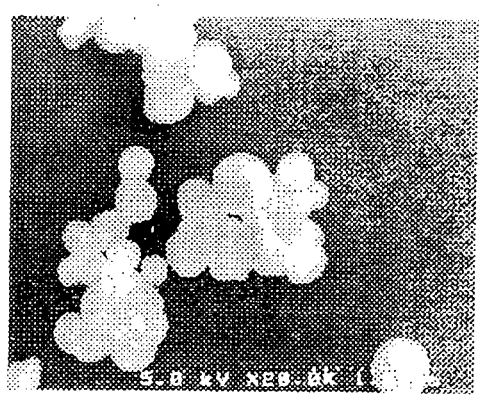

CORE-SHELL PARTICLE INCLUDING SIGNAL-GENERATING SUBSTANCE ENCLOSED THEREIN AND PROCESS FOR PRODUCING THE SAME

TECHNICAL FIELD

The present invention relates to a core-shell particle including a signal-generating substance therein and a process for producing the same. The core-shell particle including a signal-generating substance therein according to the present invention has a detectable substance included inside the particle having a water-soluble polymer compound [for example, polyethyleneglycol (PEG)] having a reactive functional group on its surface layer resembling bristles of a brush (shell), and a reactive residue that can bind to other substances at the utmost outer layer of the shell, allowing the use thereof as an easy-to-use and high-sensitivity labeling substance.

BACKGROUND ART

Various labeling agents have hitherto been developed for a visualization or quantification of trace amounts of compounds. Radioisotopes such as tritium, radioiodine, and others have been used as typical labeling agents, particularly in fields that demand a high-sensitivity, and quantified, for example, by exposure to photographic film or a measurement of radioactivity in a scintillation counter.

More recently, enzyme immunoassays have been developed as a method not influenced by a restriction imposed by handling radioactive materials. Development of the methods for labeling antigens or antibodies such as persoxidase, alkaline phosphatase, glucose oxidase, β-D-galactosidase, or the like established a quantification method suitable for enzyme immunoassay or observation of sections of tissues by staining.

On the other hand, as a method for observing sections of tissues, the method is known of labeling antibodies with a fluorescent substance (for example, fluorescein, rhodamine, or the like), and observing under a fluorescence microscope after the reaction. This method has many advantages in that the use thereof is not restricted, as it does not use radioactive substances, and that there is no need for an additional step of adding a substrate as in the enzyme-based assays, but also has a drawback in that the absolutely sensitivity thereof is not high enough for use as a labeling assay.

One of the most advanced forms of the fluorescence labeling method is the time-resolved fluorescence measurement. This is a method in which the accuracy and sensitivity of measurement is raised by irradiating pulsed excitation light to fluorescent substances that have a long fluorescence quenching time, such as an europium chelate; measuring the fluorescence after a certain period of time when the direct excitation light and short-lived fluorescence derived from the surrounding substances have been quenched; and then measuring the fluorescence specific to europium.

An attempt to raise the sensitivity further by including this europium chelate in a polystyrene particle and thus increasing the amount of fluorescent substance per particle has been made. Although this method can raise the amount of fluorescence per particle, it also has a drawback in that the resulting particle has a hydrophobic surface, as polystyrene per se is hydrophobic, and thus, when used in biological reactions, it absorbs a large number of clingy hydrophobic substances present in the environment, and thus the method should be used while considering this disadvantage.

Alternatively for the purpose of pursuing convenience rather than raising sensitivity, an attempt was also made to visually detect polystyrene particles immobilized by antigen-antibody reaction, by preparing a reagent by including a dye in a polystyrene particle and coating an antigen or antibody on the surface of the polystyrene particle.

Even though the methods known in the art of making such labeling substances by including dye or fluorescent substances in a polystyrene particle are advantageous in that they are easy to operate or provide a significantly high sensitivity, they are still accompanied by occasional errors in determination due to nonspecific reactions, even after an attempt to overcome the disadvantages of using the polystyrene particles having a hydrophobic surface, for example, by: (1) after binding a desired functional molecule such as antigen, antibody, or the like, covering the hydrophobic surface of the polystyrene with a substance such as a protein or a biological substance-resembling substance by coating it on the non-bonded surface thereof; or (2) adding a surfactant to the reaction liquid and preventing a mutual interaction between polystyrene particles.

Accordingly, the methods of using a polystyrene particle as a carrier could not overcome the disadvantage in sensitivity and specificity, even when the particle was stabilized with a blocking agent or an additive was introduced into the buffer solution during reaction, to suppress non-specific reactions.

DISCLOSURE OF THE INVENTION

An object of the present invention is to provide a particle including a signal-generating substance therein that can be used as a labeling substance, is not affected by non-specific reactions with, for example, environmental substances and biological components, has high-sensitivity, and can be prepared conveniently, and a process for producing the same.

The object above can be achieved by the core-shell particle including a signal-generating substance therein according to the present invention, wherein the core-shell particle consists of (1) a core portion substantially made of a water-insoluble polymer compound; and (2) a shell portion substantially made of a water-soluble polymer compound having a reactive-functional group, and covering a surface of the core portion in the manner of bristles of a brush; and the core portion and the shell portion are, as a whole, a block copolymer of a water-insoluble polymer and a water-soluble polymer, characterized in that the signal-generating substance is included in the core portion.

In addition, the present invention relates to a process for producing the core-shell particle including a signal-generating substance therein, characterized by immersing
(a) a core-shell particle consisting of (1) a core portion substantially made of a water-insoluble polymer compound; and (2) a shell portion substantially made of a water-soluble polymer compound having a reactive functional group, and covering a surface of the core portion in the manner of bristles of a brush; the core portion and the shell portion being a block copolymer of a water-insoluble polymer and a water-soluble polymer as a whole, and
(b) a signal-generating substance in a solution containing an organic solvent capable of swelling the water-insoluble polymer compound, to include the signal-generating substance in the core portion.

BRIEF DESCRIPTION OF THE DRAWINGS

FIG. 1 shows a $^1$H-NMR spectrum of the block copolymer prepared in EXAMPLE (1).

FIG. 2 shows a scanning electron microscope (SEM) photograph of the PEG-coated particles having aldehyde terminals obtained in EXAMPLE 1(2).

FIG. 3 shows an SEM photograph of the PEG-coated particles having aldehyde terminals for comparison obtained in EXAMPLE 1(2).

BEST MODE FOR CARRYING OUT THE INVENTION

Figure 4:
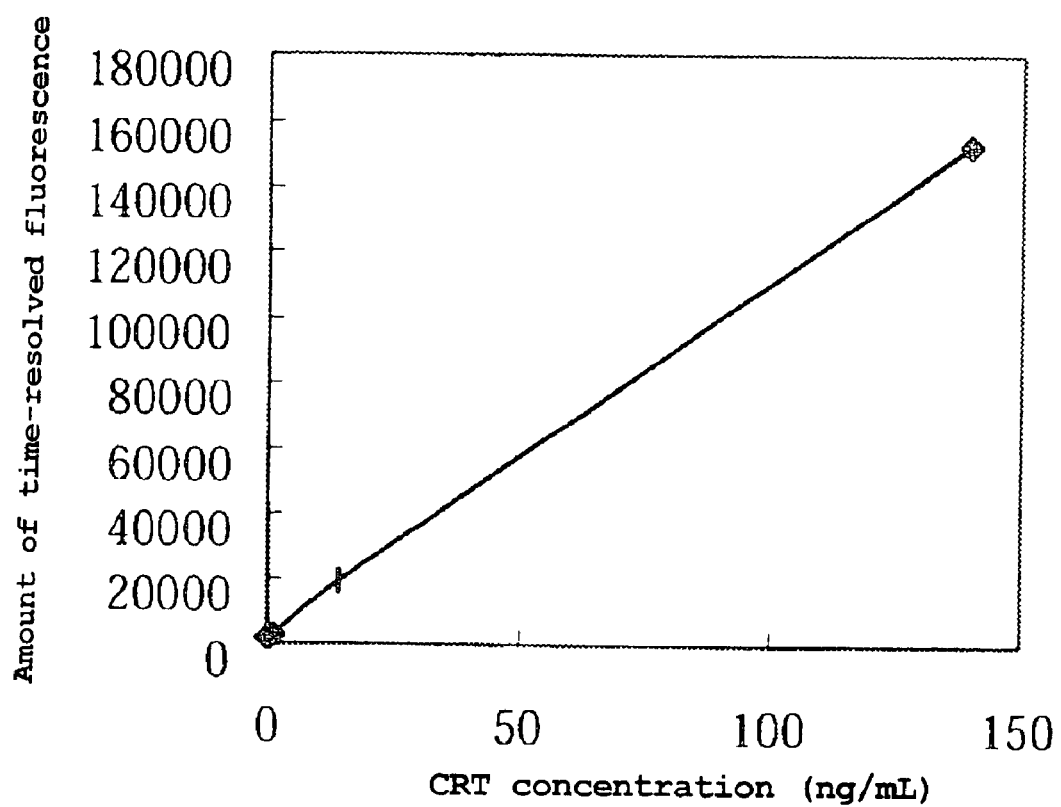
FIG. 4 illustrates a graph indicating the results of CRP measurement by the immunoassay using a europium chelate-included particle.

Hereinafter, the present invention will be described in more detail.

A core-shell particle consisting of (1) a core portion substantially made of a water-insoluble polymer compound; and (2) a shell portion substantially made of a water-soluble polymer compound having a reactive functional group, and covering a surface of the core portion in the manner of bristles of a brush, i.e., a core-shell particle which, on the surface of the core portion substantially made of a water-insoluble polymer compound, has a water-soluble polymer compound brush having a reactive functional group on the outer layer thereof per se is known.

The water-insoluble polymer compound that can be used for forming the core portion in the present invention is not particularly limited, so long as it is a water-insoluble polymer compound which can accommodate a signal-generating substance within the core portion when it is formed. Examples of the water-insoluble polymer compound include: hydrophobic polymers [for example, polystyrene, polymethyl methacrylate, poly(2-hydroxyethyl methacrylate), poly(N-isopropyl acrylamide) polyisoprene, polyvinyl chloride, polylactic acid, polylactone, or polylactam], crosslinked gels of water-soluble polymers (for example, polyvinylalcohol, polyacrylamide, polydimethyl acrylamide, polyallylamine, or polyacrylic acid); or water-insoluble natural polymer compounds (for example, gelatin or polysaccharides).

In the present invention, the core portion may be substantially formed from only one of the water-insoluble polymer compounds or from a combination of two or more water-insoluble polymer compounds.

The shape of the core portion is not particularly limited, but in general is almost spherical or almost oval. In addition, the dimensions of the core portion are not particularly limited and may be changed according to desired use. The diameter of the core portion of spherical particle is generally approximately 5 to 500 nm.

The water-soluble polymer compound that can be used for forming the shell portion in the present invention is not particularly limited, so long as it is a straight chain polymer compound that can bind to the surface of the core portion at one terminal (binding terminal) and has a reactive functional group or a group to which a reactive functional group can be introduced at the other terminal (free terminal) and can be arranged into the shape of bristles of a brush covering the surface of the core portion. The "shell portion covering the surface of the core portion in the manner of bristles of a brush" as used herein means that the shell portion includes a great number of straight chain water-soluble polymer compounds, each of the straight chain water-soluble polymer compounds binding to the surface of the core portion at the binding terminal, and the free terminal thereof sticking out like a bristle or a rod into the reaction solution wherein at least the water-soluble polymer compound and a substance to be introduced (for example, antigen or antibody) are reacted. In addition, as these brush-like water-soluble polymer compound chains have respectively reactive functional groups at the free terminal that can bind to the substance to be introduced [for example, physiologically active substance (for example, antibody, enzyme, or DNA)], the utmost outer layer of the shell portion is covered with a large number of the reactive functional groups.

The water-soluble polymer compound may be, for example, polyethyleneglycol (PEG), polyvinylalcohol, polyvinylpyrrolidone, polyamino acid, polyacrylic acid, polydimethylaminoethyl methacrylate, polyallylamine, or the like, and preferably PEG or polyvinyl alcohol.

In the present invention, as for the water-soluble polymer compound chains constituting the shell portion, each of the water-soluble polymer compound chains may be substantially formed from only one of the water-soluble polymer compounds, or from a combination of two or more mutually different water-soluble polymer compounds.

Preferably, the water-soluble polymer compound chains constituting the shell portion substantially cover the entire surface of the core portion. In addition, it is preferable that each of the water-soluble polymer compound chains constituting the shell portion has essentially the same length and the outer layer surface of the almost spherical or oval shell is formed by the free terminals of the water-soluble polymer compound chains.

The ratio of the diameter of the core portion and the thickness of the shell portion may be varied according to the use. For example, the diameter of the core portion may be, for example, 5 to 500 nm and the thickness of the shell portion, for example, 5 to 500 nm.

The reactive functional group at the free terminal of the water-soluble polymer compound chain may be present at one terminal (free terminal) of the water-soluble polymer compound before another terminal (binding terminal) thereof is bound to the surface of the core portion, or alternatively, may be introduced, after one terminal (binding terminal) of the water-soluble polymer compound is bound to the surface of the core portion, to another terminal (free terminal). These reactive functional groups are not particularly limited, so long as the functional groups are all stable in water (or aqueous solvent) and can react with a substance to be introduced [for example, physiologically active substance (for example, antibody, enzyme, or DNA)] required when the core-shell particle including a signal-generating substance therein according to the present invention is used as a labeling substance, and examples thereof include, for example, aldehyde, carboxyl, mercapto, amino, maleimide, vinylsulfone, and methanesulfonyl groups, and preferably, aldehyde, amino, carboxyl, and maleimide groups.

A variety of processes known in the art may be applied as the method for preparing the core-shell particle which, on the surface of the core portion substantially made of a water-insoluble polymer compound, has a water-soluble polymer compound brush having a reactive functional group on the outer layer thereof. The known process may be for example:

(1) an emulsion method wherein particles are prepared by mixing (a) a block copolymer (hydrophilic/hydrophobic block copolymer) consisting of a hydrophilic segment containing a reactive functional group and a hydrophobic segment bound to each other, and (b) a hydrophobic polymer;

(2) a dispersion polymerization method wherein a hydrophobic monomer is polymerized using a water-soluble polymeric macromonomer having a reactive functional group as a dispersant; or (3) a method of introducing brush-like bristles of a water-soluble polymer compound on the surface of a hydrogel particle.

As the method for preparing the hydrophilic/hydrophobic block copolymer used in the above emulsion method (1) and the method for preparing the water-soluble polymeric macromonomer having a reactive functional group used in the above dispersion method (2), for example, the method developed by the present inventors and the co-developers (for example, WO 96/33233, WO 99/57174, or Japanese Unexamined Patent Publication (Kokai) No. 11-322917) may be used.

Compounds that may be used as the hydrophilic/hydrophobic block copolymer or water-soluble polymeric macromonomer may be, for example, the heterotelechelic block copolymers described in WO 96/33233 of the formula (IA):

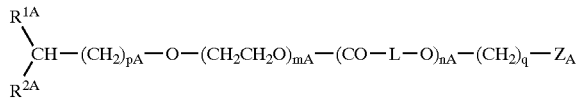

(IA)

[wherein, $R^{1A}$ and $R^{2A}$ are independently an alkoxy group having 1 to 10 carbon atoms, an aryloxy group, or an aryl-(alkyloxy having 1 to 3 carbon atoms) group; $R^{1A}$ and $R^{2A}$ together form an ethylenedioxy group, which may be substituted with an alkyl group having 1 to 6 carbon atoms, of the formula:

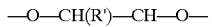

(wherein, R' is a hydrogen atom or an alkyl group having 1 to 6 carbon atoms); or $R^{1A}$ and $R^{2A}$ together form oxy (=O); and L is a divalent group of the formula:

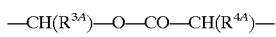

or

wherein $R^{3A}$ and $R^{4A}$ are independently a hydrogen atom, an alkyl group having 1 to 10 carbon atoms, an aryl group, or an aryl-alkyloxy group having 1 to 3 carbon atoms; r is an integer of 2 to 5; $m_A$ is an integer of 2 to 10,000; $n_A$ is an integer of 2 to 10,000; $p_A$ is an integer of 1 to 5; q is an integer of 0 or 1 to 20; and $Z_A$ is a hydrogen atom, an alkali metal, an acetyl, acryloyl, methacroyl, cinnamoyl, p-toluenesulfonyl, 2-mercaptopropionyl, 2-aminopropionyl, allyl, or vinylbenzyl group when q is 0, and an alkoxycarbonyl group having 1 to 6 carbon atoms, a carboxylmercapto or amino group when q is an integer of 1 to 20]. The heterotelechelic block copolymers of the formula (IA) may be prepared, for example, by the method described in WO 96/33233.

In addition, the compounds that may be used as the hydrophilic/hydrophobic block copolymer or water-soluble polymeric macromonomer may be, for example, the polyoxyethylene derivative described in WO 99/57174 of the formula (TB):

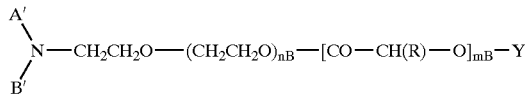

(wherein, A' and B' are independently an amino protecting group of an organic silyl type, or amino protecting groups of an organic silyl type that may form together with the nitrogen atom to which A' and B' bind a 4- to 7-membered disila-azacyclo heterocyclic ring; Y is a hydrogen atom, an alkali metal, or an organic group which can be introduced by a suitable reaction replacing the alkali metal; R is a hydrogen atom or an alkyl having 1 to 6 carbon atoms; $n_B$ is an integer of 1 to 20,000; and ma is an integer of 0 to 20,000). The polyoxyethylene derivative of the formula (IB) may be, for example, prepared by the method described in WO 99/57174.

The compounds that can be used as the hydrophilic/hydrophobic block copolymer or water-soluble polymeric macromonomer further include, for example, compounds containing an organic silyl sulfide group and polyoxyethylene derivatives described in Japanese Unexamined Patent Publication (Kokai) No. 11-322917 of the formula (IC):

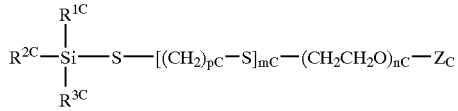

(wherein, $R^{1C}$, $R^{2C}$, and $R^{3C}$ are independently a straight chain or branched alkyl group or an aralkyl group; $Z_C$ is a functional group selected from the group consisting of a hydrogen atom, acryloyl, methacryloyl, vinylbenzyl, allyl, para-toluenesulfonyl groups, a mono- or di-lower alkyl substituted amino group, an alkyl group having a carboxyl group or the ester group thereof, an alkyl group having an aldehyde group or the acetal group thereof, and an alkali metal; $m_c$ is 0 or 1; $n_c$ is an integer of 0 to 20,000; and, $p_c$ is a positive integer of 2 or 3; with the proviso that $m_c$ and $n_c$ are not 0 at the same time). The compounds containing an organic silylsulfide group or polyoxyethylene derivatives represented by formula (IC) can be prepared, for example, by the method described in Japanese Unexamined Patent Publication (Kokai) No. 11-322917.

According to the above emulsion method (1) for preparing core-shell particles, a core-shell particle (i.e., a particle before a signal-generating substance is included) can be prepared by mixing the compound of the formula (IA), (IB), or (IC) (i.e., hydrophilic/hydrophobic block copolymer) and a hydrophobic polymer.

According to the above dispersion method (2) for preparing core-shell particles, a core-shell particle (i.e., a particle before a signal-generating substance is included) can be prepared by polymerizing a hydrophobic monomer using the compound of the formula (IA), (IB), or (IC) (i.e., water-soluble polymeric macromonomer) as a dispersant.

The signal-generating substance that can be used in the present invention is not particularly limited, so long as it can generate a signal that can be analyzed (including detection and measurement) from outside the core-shell particle even when it is in the state of inclusion in the core portion, and examples thereof include fluorescent substances, light-emitting substances, and dyes.

Examples of the fluorescent substance include lanthanoid chelates (for example, lanthanum chelate, cerium chelate, praseodymium chelate, neodymium chelate, promethium chelate, samarium chelate, europium chelate, gadolinium chelate, terbium chelate, dysprosium chelate, holmium chelate, erbium chelate, thulium chelate, ytterbium chelate, or lutetium chelate, preferably europium chelate or terbium chelate), fluoroscein isocyanate, dichlorotriazinylfluoroscein, or tetramethylrhodamine isocyanate.

The dye may be, for example, methyl yellow, Solvent Blue 35, Oil Orange SS, or Oil Red EGN.

The diameter of the core-shell particle including a signal-generating substance therein may also be varied according to desired use. It is usually approximately 10 nm to 1 mm when the particle is almost spherical.

The core-shell particle including a signal-generating substance therein according to the present invention can be prepared by, for example, the process of the present invention.

In the process of the present invention, for example, in order to include a signal-generating substance in the core-shell particle (i.e., particle before a signal-generating substance is included) prepared by various known processes described above, the core-shell particle and a signal-generating substance (for example, dye, fluorescent substance, or the like having a hydrophobic property) are first immersed in a solution that contains a certain amount of an organic solvent (for example, acetone, toluene, or the like) that swells the water-insoluble polymer compound forming the core portion of the core-shell particle. The water-insoluble polymer compound swells by immersion and incorporates the signal-generating substance into the core portion during the swelling. Subsequently, when the organic solvent is removed from the mixture, the water-insoluble polymer compound shrinks, and accordingly, the hydrophobic signal-generating substance becomes unable to migrate out of the core portion and is included in the core portion. The core-shell particles including a signal-generating substance therein of the present invention can be prepared by removing the signal-generating substance that is not included in the core portion, if desired.

In the process of the present invention, the method for removing organic solvent from the mixture is not particularly limited, but there may be mentioned, for example, a method to evaporate the organic solvent to dryness by evaporation, or a method of shrinkage in a nonsolvent (for example, by replacing the solution containing the organic solvent with a solution containing no organic solvent).

The ratio of the organic solvent in the solution containing an organic solvent used for swelling the core portion is not particularly limited, so long as the ratio is sufficient for swelling the water-insoluble polymer compound to an extent such that the signal-generating substance is incorporated into the water-insoluble polymer compound, but may be, for example, 40 to 60 (vol/vol)%.

In the present invention, a substance to be introduced (for example, physiologically active substance) that can react with the reactive functional group may additionally be bound to the reactive functional groups present on the surface of the core-shell particle including a signal-generating substance therein according to the present invention.

The substance to be introduced is not particularly limited, so long as it can react with the reactive functional groups present on the surface of the core-shell particle including a signal-generating substance therein, and examples thereof include physiologically active substances such as proteins (for example, antibodies and enzymes), nucleic acids (for example, DNAs and RNAs), cells, or the like.

The method for binding the substance to be introduced to the reactive functional groups present on the surface of the core-shell particle including a signal-generating substance therein may be selected suitably from known binding methods according to the kind of substance to be introduced, and the reactive functional group.

For example, when the reactive functional group is an aldehyde group, the functional group may be bound to a physiologically active substance [for example, protein (for example, antigen, antibody, receptor, or the like), peptide, low molecular weight hormone, DNA, or the like] by forming a Schiff base with an amino group therein.

When the reactive functional group is a carboxyl group, the group can be bound to an amino group of a physiologically active substance using a condensation agent (for example, carbodiimide or the like). Alternatively, the carboxyl group may be first activated with a compound such as succinimide, maleimide, or the like and bound to the physiologically active substance by mixing.

EXAMPLES

Hereinafter, the present invention will be described in detail with reference to EXAMPLES, but the scope of the present invention is not limited thereto.

Example 1

(1) Synthesis of acetal-PEG-PLA-methacryloyl

Into a reaction vessel containing 40 mL of tetrahydrofuran (THF) as a solvent at room temperature under an argon atmosphere, were added 0.32 mL (2 mmol) of 3,3'-diethoxy-1-propanol and then 6.2 mL (2 mmol) of 0.3263 mol/L potassium naphthalene THF solution, and the resulting mixture was stirred for 15 minutes for metalation. Additionally, 12 mL (240 mmol) of ethylene oxide was added via a cooled syringe, and the resulting mixture was stirred at room temperature for 2 days to conduct a ring-opening polymerization. Then, 84 mL (84 mmol) of 1 mol/L DL-lactide THF solution was added, and polymerized at room temperature for 3 hours. Additionally, 4.5 mL (28 mmol) of anhydrous methacrylic acid was added. After the mixture was stirred at room temperature for 2 days, the polymerization was terminated.

The block copolymer solution thus obtained was poured into 2-propanol previously cooled to −15° C., and the precipitated polymer was centrifuged (6000 rpm, 40 minutes, −10° C.) to remove the solvent. Thereafter the block copolymer was further purified by repeating this procedure twice, being dissolved in benzene, and lyophilized.

FIG. 1 shows the $^1$H-NMR spectrum of the block copolymer. The molecular weight of polyethyleneglycol (PEG) was calculated based on the result of GPC measurement. The molecular weight of polylactic acid (PLA) was calculated from the result of $^1$H-NMR, together with the molecular weight of PEG obtained by the GPC measurement above. The PEG had a molecular weight of approximately 5,000 and the PLA approximately 500.

(2) Preparation of an Aldehyde-Functionalized PEG-Coated Particle

Into a reaction vessel containing 160 mL of ultrapure water, in which argon replacement had been previously performed, at room temperature under an argon atmosphere, a solution of 30 mg of azobisisobutyronitrile (AIBN) and 3.4 g of the block copolymer [prepared in EXAMPLE 1(1)] in 2 mL of styrene was, after deaeration by bubbling argon, added dropwise while stirring (400 rpm).

After stirring at room temperature for 30 minutes, the solution was further stirred at 60° C. for 18 hours and additionally at 80° C. for 6 hours (400 rpm) to complete polymerization. After the polymerization reaction, resin masses and foreign particles were removed by filtration through a filter paper [Filter paper 2 (diameter: 185 mm); Advantec] to give particles having acetal groups in the surface layer (acetal functionalized particles). After the particles were dispersed in water, the dispersion containing the particles was adjusted to pH 2.0 with 1 mol/L HCl and stirred for 2 hours. Subsequently, the dispersion was made to pH 5.0 with 1 mol/L NaOH to deprotect the protecting acetal groups and introduce aldehyde groups to the surface area.

Then, for demineralization, 100 mL of the particle dispersion was dialyzed against 2 L of distilled water for 1 day [molecular weight cut off (MWCO): 12,000 to 14,000; distilled water exchanged 4 times], and filtered through a filter paper [Filter paper 2 (diameter: 185 mm); Advantec] to give particles having aldehyde groups in the surface layer (aldehyde functionalized particles), i.e., aldehyde-functionalized block polymer styrene particles (particle diameter: 65 nm). The scanning electron microscope (SEM) photograph of the particle (molecular weight of the PEG: approximately 5,000; that of PLA: approximately 500) thus obtained is shown in FIG. 2.

In addition, by repeating the procedures of EXAMPLEs 1(1) and 1(2) except that anhydrous methacrylic acid was added without using the DL-lactide THF solution after the ring-opening polymerization of ethylene oxide in EXAMPLE 1(1), comparative particles having a PLA unit of a different length (molecular weight of PEG: approximately 5,000; that of PLA: 0) were prepared. The SEM photograph of the comparative particle is shown in FIG. 3.

(3) Preparation of a Europium Chelate-Included Particle

To 1 mL of an aqueous solution of europium chloride hexahydrate (22 mg/mL, distilled water), 1 mL of a solution of thienoyltrifluoroacetone (TTA) in acetone (37 mg/mL), and further 2 mL of a trioctylphsophinoxide (TOPO) solution in acetone (43.5 mg/mL) were added to give a europium chelate solution.

Separately, to 5 mL of a suspension containing the aldehyde-functionalized block polymer styrene particles (particle diameter: 65 nm) prepared in EXAMPLE 1(2) (18 mg/mL, distilled water), 5 mL of acetone was added and stirred. To the liquid mixture, 0.12 mL of the europium chelate solution previously prepared was added, and the mixture was stirred for an additional 10 seconds. After stirring, the mixture was allowed to stand at room temperature while protected from light for 30 minutes, and then purged with nitrogen gas to remove acetone. Subsequently, the solution was filtered through a 0.2 $\mu$m filter to remove the europium chelate not incorporated into the particles and precipitated by the removal of acetone, providing the europium chelate-included particles according to the present invention.

Example 2

(1) Preparation of Anti-CRP Antibodies Labeled with Europium-Included Particle

To 0.5 mL of the europium-included particles prepared in EXAMPLE 1, 0.5 mL of 0.2 mol/L phosphate buffer (pH 8.0) was added and stirred, afterward, 0.1 mL of anti-C-reactive protein (CRP) rabbit antibody F(ab')$_2$ fraction (20 mg/mL, physiological saline) was added and mixed, and the solution was allowed to stand at room temperature for 1 hour. The anti-CRP rabbit antibody F(ab')$_2$ fraction was prepared according to the common method from an anti-CRP rabbit antibody (Dako). To the reaction solution, 12 mg of NaBCNH$_3$ was added and stirred at room temperature for 15 hours.

The reaction solution was applied onto a Sephacryl S-300 column (1 cm×45 cm; Pharmacia) previously equilibrated with a 50 mM Tris-HCl buffer solution (pH 7.8) containing 0.15 M sodium chloride, and fractioned into tubes (1 mL/tube) at a flow rate of 10 mL/hour.

By monitoring the UV absorbance, the peak of particles first eluted were collected as the anti-CRP antibody labeled with the europium-included particle.

(2) Measurement of CRP by Immunoassay Using the Anti-CRP Antibody Labeled with Europium-Included Particle Into each well on a 96-well plate for ELISA, 50 mL of the anti-CRP rabbit antibody F(ab')$_2$ fraction diluted to a concentration of 4 $\mu$g/mL with physiological saline was pipetted and allowed to stand at 4° C. overnight to coat. After each well was washed three times with a 1/15 mol/L phosphate buffer (PBS; pH 7.4), 0.25 mL of PBS containing 1% bovine serum albumin (BSA) was pipetted into each well, and blocking was performed at 37° C. for 1 hour.

After each well was washed three times with a 1/15 mol/L PBS (pH 7.4), 50 $\mu$L of a CRP standard sample diluted with a 50 mM Tris-HCl buffer solution (pH 7.5) containing 0.1% Tween 20 and 0.15 M sodium chloride was pipetted into each well, and the mixture was subjected to a reaction at 37° C. for 1 hour.

After each well was washed three times with a 1/15 mol/L PBS (pH 7.4), 50 mL of a dilute solution of the anti-CRP antibody labeled with europium-included particles prepared in EXAMPLE 2(1) [1000 times diluted with a 50 mM Tris-HCl buffer solution (pH 7.5) containing 0.1% Tween 20, 0.2% BSA, and 0.15 M sodium chloride] was pipetted into each well and the mixture was subjected to a reaction at 37° C. for 1 hour.

After each well was washed 5 times with 1/15 mol/L PBS (pH 7.4), the amount of time-resolved fluorescence of the plate was determined for 1 second by a time-resolved fluorophotometer (Wallac). The results are summarized in TABLE 1 and FIG. 4.

TABLE 1

| Conc. of CRP antigen (ng/mL) | Time-resolved fluorescence |
| --- | --- |
| 0 | 1611 |
| 0.14 | 1713 |
| 1.4 | 2566 |
| 14 | 19259 |
| 140 | 152695 |

INDUSTRIAL APPLICABILITY

The particle including a signal-generating substance therein according to the present invention can be used as a labeling substance for physiologically active substances, and allows a high-sensitivity and specific detection of analytes by conducting a binding reaction using the activity of the physiologically active substances and subsequently detecting signals generated by the signal-generating substance. Accordingly, the particle including a signal-generating substance therein can be used in a wide range of applications as a safe, easy-to-use, and excellent labeling substance.

Currently, there are numerous substances that requires a high-sensitivity assay, including low molecular weight substances such as agricultural chemicals and environment hormones (endocrine disrupters), antigens or antibodies released into body fluids when there are abnormalities in the body or antigens derived from viruses that have invaded the body, antibodies thereto, DNAs or RNAs, and the like. For that purpose, methods of quantifying these substances by connecting a labeling agent, such as a radioisotope, enzyme, fluorescent substance, dye or the like, to a substance that binds to a desired analyte, and measuring by some means have been developed. The particle including a signal-generating substance therein according to the present invention is a labeling substance having a superior sensitivity, easy-to-use, paucity of nonspecific reaction, and the like than other known labeling substances.

Although the present invention has been described with reference to specific embodiments, various changes and modifications obvious to those skilled in the art are possible without departing from the scope of the appended claims.

What is claimed is:

1. A core-shell particle including a signal-generating substance therein, wherein the core-shell particle consists of
   (1) a core portion substantially made of a water-insoluble polymer compound; and
   (2) a shell portion substantially made of a water-soluble polymer compound having a reactive functional group, and covering a surface of the core portion in the manner of bristles of a brush; and
   the core portion and the shell portion are, as a whole, a block copolymer of a water-insoluble polymer and a water-soluble polymer,
   characterized in that the signal-generating substance is included in the core portion.

2. The core-shell particle including a signal-generating substance therein according to claim 1, wherein the water-soluble polymer compound is polyethyleneglycol.

3. The core-shell particle including a signal-generating substance therein according to claim 2, wherein the water-insoluble polymer compound is polystyrene.

4. The core-shell particle including a signal-generating substance therein according to claim 2, wherein the reactive functional group is an aldehyde, amino, carboxy, maleimide, or succinimide group.

5. The core-shell particle including a signal-generating substance therein according to claim 2, wherein the signal-generating substance is a dye.

6. The core-shell particle including a signal-generating substance therein according to claim 2, wherein the signal-generating substance is a fluorescent substance.

7. The core-shell particle including a signal-generating substance therein according to claim 2, wherein the signal-generating substance is a lanthanoid chelate.

8. The core-shell particle including a signal-generating substance therein according to claim 1, wherein the water-insoluble polymer compound is polystyrene.

9. The core-shell particle including a signal-generating substance therein according to claim 8, wherein the reactive functional group is an aldehyde, amino, carboxy, maleimide, or succinimide group.

10. The core-shell particle including a signal-generating substance therein according to claim 8, wherein the signal-generating substance is a dye.

11. The core-shell particle including a signal-generating substance therein according to claim 8, wherein the signal-generating substance is a fluorescent substance.

12. The core-shell particle including a signal-generating substance therein according to claim 8, wherein the signal-generating substance is a lanthanoid chelate.

13. The core-shell particle including a signal-generating substance therein according to claim 1, wherein the reactive functional group is an aldehyde, amino, carboxy, maleimide, or succinimide group.

14. The core-shell particle including a signal-generating substance therein according to claim 13, wherein the signal-generating substance is a dye.

15. The core-shell particle including a signal-generating substance therein according to claim 13, wherein the signal-generating substance is a fluorescent substance.

16. The core-shell particle including a signal-generating substance therein according to claim 13, wherein the signal-generating substance is a lanthanoid chelate.

17. The core-shell particle including a signal-generating substance therein according to claim 1, wherein the signal-generating substance is a dye.

18. The core-shell particle including a signal-generating substance therein according to claim 1, wherein the signal-generating substance is a fluorescent substance.

19. The core-shell particle including a signal-generating substance therein according to claim 1, wherein the signal-generating substance is a lanthanoid chelate.

20. A process for producing the core-shell particle including a signal-generating substance therein according to claim 1, characterized by immersing
   (a) a core-shell particle consisting of (1) a core portion substantially made of a water-insoluble polymer compound; and (2) a shell portion substantially made of a water-soluble polymer compound having a reactive functional group, and covering a surface of the core portion in the manner of bristles of a brush; the core portion and the shell portion being a block copolymer of a water-insoluble polymer and a water-soluble polymer as a whole, and
   (b) a signal-generating substance in a solution containing an organic solvent capable of swelling the water-insoluble polymer compound, to include the signal-generating substance in the core portion.

* * * * *

UNITED STATES PATENT AND TRADEMARK OFFICE
CERTIFICATE OF CORRECTION

PATENT NO. : 6,881,484 B2
DATED : April 19, 2005
INVENTOR(S) : Kazunori Kataoka et al.

It is certified that error appears in the above-identified patent and that said Letters Patent is hereby corrected as shown below:

<u>Title page,</u>
Item [73], Assignee, should read -- NanoCarrier --.
Item [22], PCT Filed, should read -- May 30, 2002 --.
Item [87], PCT Pub. No., should read -- W002/97436 --.
Item [87], PCT Pub. Date, should read -- December 5, 2002 --.

<u>Column 5,</u>
Lines 65-67, should read
-- In addition, the compounds that may be used as the hydrophilic/hydrophobic block copolymer or water-soluble polymeric macromonomer may be, for example, the polyoxyethylene derivative described in WO 99/571743 of the formula (IB): --.

<u>Column 6,</u>
Line 5 should read

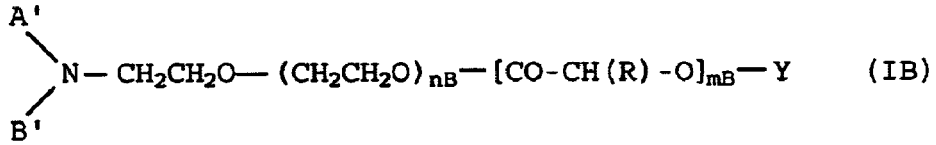

Lines 9-15, should read
-- (wherein, A' and B' are independently an amino protecting group of an organic silyl type, or amino protecting groups of an organic silyl type that may form together with the nitrogen atom to which A' and B' bind a 4- to 7-membered disila-azacyclo heterocyclic ring; Y is a hydrogen atom, an alkali metal, or an organic group which can be introduced by a --.

Signed and Sealed this

Twenty-seventh Day of September, 2005

JON W. DUDAS
*Director of the United States Patent and Trademark Office*